(12) United States Patent
Berner et al.

(10) Patent No.: US 7,736,667 B2
(45) Date of Patent: Jun. 15, 2010

(54) SHELL-AND-CORE DOSAGE FORM APPROACHING ZERO-ORDER DRUG RELEASE

(75) Inventors: Bret Berner, El Granada, CA (US); Jenny Louie-Helm, Union City, CA (US); Gloria Gusler, Cupertino, CA (US); John N. Shell, Rocklin, CA (US)

(73) Assignee: Depomed, Inc., Menlo Park, CA (US)

( * ) Notice: Subject to any disclaimer, the term of this patent is extended or adjusted under 35 U.S.C. 154(b) by 103 days.

(21) Appl. No.: 10/213,823

(22) Filed: Aug. 7, 2002

(65) Prior Publication Data

US 2003/0104062 A1 Jun. 5, 2003

Related U.S. Application Data

(63) Continuation of application No. 09/498,945, filed on Feb. 4, 2000, now abandoned.

(51) Int. Cl.
A61K 9/52 (2006.01)
A61K 9/20 (2006.01)
A61K 9/22 (2006.01)
A61K 9/24 (2006.01)
A61K 9/28 (2006.01)

(52) U.S. Cl. .............. 424/457; 424/468; 424/464; 424/474; 424/472

(58) Field of Classification Search ........... 424/469, 424/468, 422, 472, 457, 464, 474; 514/772.3, 514/779
See application file for complete search history.

(56) References Cited

U.S. PATENT DOCUMENTS

| | | | |
|---|---|---|---|
| 4,088,798 A | 5/1978 | Michaelis | |
| 4,309,406 A * | 1/1982 | Guley et al. | 424/489 |
| 4,629,620 A | 12/1986 | Lindahl et al. | |
| 4,756,911 A | 7/1988 | Drost et al. | |
| 4,789,549 A | 12/1988 | Khan | |
| 4,816,264 A | 3/1989 | Philips et al. | |
| 4,891,223 A | 1/1990 | Ambegaonkar | |
| 4,892,742 A | 1/1990 | Shah | |
| 5,151,273 A | 9/1992 | Korsatko-Wabnegg et al. | |
| 5,190,760 A * | 3/1993 | Baker | 424/438 |
| 5,391,378 A | 2/1995 | Sanderson | |
| 5,458,887 A | 10/1995 | Chen et al. | |
| 5,458,888 A | 10/1995 | Chen | |
| 5,464,633 A | 11/1995 | Conte et al. | |
| 5,500,227 A | 3/1996 | Oshlack et al. | |
| 5,549,913 A | 8/1996 | Colombo et al. | |
| 5,654,005 A | 8/1997 | Chen et al. | |
| 5,736,159 A | 4/1998 | Chen et al. | |
| 5,783,212 A | 7/1998 | Fassihi et al. | |
| 5,827,538 A | 10/1998 | Cussler et al. | |
| 5,840,332 A | 11/1998 | Lerner et al. | |
| 5,861,173 A | 1/1999 | Nishioka et al. | |
| 5,876,752 A | 3/1999 | Herbig et al. | |
| 5,891,474 A | 4/1999 | Busetti et al. | |
| 5,916,595 A | 6/1999 | Chen et al. | |
| 5,955,106 A | 9/1999 | Moeckel et al. | |
| 5,972,389 A | 10/1999 | Shell et al. | |
| 6,099,859 A | 8/2000 | Cheng et al. | |
| 6,120,803 A * | 9/2000 | Wong et al. | 424/473 |
| 6,149,940 A * | 11/2000 | Maggi et al. | 424/472 |
| 6,248,363 B1 | 6/2001 | Patel et al. | |
| 6,372,255 B1 | 4/2002 | Saslawski et al. | |
| 6,475,521 B1 * | 11/2002 | Timmins et al. | 424/469 |
| 2003/0091630 A1 * | 5/2003 | Louie-Helm et al. | 424/468 |

FOREIGN PATENT DOCUMENTS

| | | | |
|---|---|---|---|
| CA | 2220038 | * | 7/1999 |
| DE | 44 32 757 A1 | | 3/1996 |
| DE | 4432757 A1 | | 3/1996 |
| EP | 0 526 862 A1 | | 2/1993 |
| EP | 0526862 A1 | | 2/1993 |
| GB | 1 330 829 | | 9/1973 |
| GB | 1 428 426 | | 3/1976 |
| GB | 1428426 | | 3/1976 |
| WO | WO 95/08515 | | 3/1995 |
| WO | WO 98/08515 A1 | | 3/1998 |

(Continued)

OTHER PUBLICATIONS

Lee, B. "Controlled release of dual drug-loaded hydroxypropyl methylcellulose matrix tablet using drug-containing polymeric coatings," International Journal of Pharmaceutics, 1999, pp. 71-80, vol. 188.
Ghanem, A.H. et al., Pharmazie, 1979, pp. 7415-7417, vol. 34.
Kallstrand, G. and Ekman, B., Journal of Pharmaceutical Sciences, Jul. 1983, pp. 772-775, vol. 72(7).
Conte, U. et al.; "Modulation of the dissolution profiles from Geomatrix® multi-layer matrix tablets containing drugs of different solubility"; 1995, Biomaterials, vol. 17, No. 9, pp. 889-896.
Pillay et al., Journal of Controlled Release 67: 55-65 (2000).
Halsas et al., S.T.P. Pharma Sciences 8:3: 155-161 (1998).
Sirkia et al., S.T.P. Pharma Sciences 3:6: 453-458 (1993).

(Continued)

Primary Examiner—Sreeni Padmanabhan
Assistant Examiner—Umamaheswari Ramachandran
(74) Attorney, Agent, or Firm—Paul B. Simboli; Judy M. Mohr; Susan L. Harlocker

(57) ABSTRACT

Drugs are formulated as oral dosage forms for controlled release in which the release rate limiting portion is a shell surrounding the drug-containing core. The shell releases drug from the core by permitting diffusion of the drug from the core. The shell also promotes gastric retention of the dosage form by swelling upon imbibition of gastric fluid to a size that is retained in the stomach during the postprandial or fed mode.

55 Claims, 1 Drawing Sheet

FOREIGN PATENT DOCUMENTS

| | | | |
|---|---|---|---|
| WO | WO 98/55107 | * | 6/1998 |
| WO | WO 98/55107 | | 12/1998 |
| WO | WO 98/55107 A1 | | 12/1998 |
| WO | WO 99/47128 | | 9/1999 |
| WO | WO 99/47128 A1 | | 9/1999 |

OTHER PUBLICATIONS

Fukui et al., *Journal of Controlled Release* 68: 215-223 (2000).
Sirkia et al., *International Journal of Pharmaceutics* 107: 179-187 (1994).
Sirkia et al., *European Journal of Pharmaceutical Sciences* 1: 195-201 (1994).
Halsas et al., "Biopharmaceutical evaluation of time-controlled press-coated tablets containing polymers to adjust drug release", Division of Biopharmaceutics and Pharmacokinetics, University of Helsinki, 190-196.
Deshpande et al., *Pharmaceutical Research* 14:6: 815-819 (1997).
Ito et al., "Investigation of Compressed Coating Tablet Swelling with Water as New Dosage Form for Elderly Patients", 20:1: 41-48 (1994).
Baichwal, A. and Neville, D.A. "Drug Delivery Partnership: Culturing innovation and enhancing medications using oral drug delivery," *Drug Delivery Technol*. May 2002, pp. 65-68, vol. 2, No. 3.
Maggie, L. et al. "Highly swellable, multi-layer tablets to prolong the residence time of the delivery device in the stomach," *Abstracts/J. of Controlled Release* 2000, pp. 332-334, vol. 64.

* cited by examiner

SHELL-AND-CORE DOSAGE FORM APPROACHING ZERO-ORDER DRUG RELEASE

CROSS-REFERENCE TO RELATED APPLICATIONS

This application is a continuation of U.S. application Ser. No. 09/498,945, filed Feb. 4, 2000, now abandoned, the contents of which is incorporated herein by reference in its entirety.

BACKGROUND OF THE INVENTION

1. Field of the Invention

This invention is in the general field of pharmaceuticals, and relates in particular to formulations for drugs that benefit from a prolonged time of controlled release in the stomach and upper gastrointestinal (GI) tract, and from an enhanced opportunity for absorption in the stomach and upper GI tract rather than the lower portions of the GI tract. One goal of this invention is to release drugs in a controlled manner over an extended period of time. Another goal is to extend the time of delivery into the stomach of drugs that are preferentially absorbed high in the GI tract, and thereby to achieve a greater and more prolonged therapeutic effect with potentially diminished side effects. This will reduce the frequency of administration required and achieve a more efficient use of the drugs and a more effective treatment of local stomach disorders. A third goal is to minimize both lower-tract inactivation of the drug and drug effects on the lower intestinal flora.

2. Description of the Prior Art

Drugs that are administered in the form of conventional tablets or capsules become available to body fluids at a rate that is initially very high, followed by a rapid decline. For many drugs, this delivery pattern results in a transient overdose, followed by a long period of underdosing. This is a pattern of limited clinical usefulness. Improved delivery patterns were first made available in the 1970's with the introduction of a variety of controlled delivery systems. These systems lowered the amount of drug released immediately after dosing and extended the time period over which drug release continued, thereby minimizing both the overdose and the underdose effects. These improvements provided effective medication with reduced side effects, and achieved these results with reduced dosing frequency.

Many of these controlled delivery systems utilize hydrophilic, polymeric matrices that provide useful levels of control to the delivery of drugs. Such matrices do not provide adequate control over the drug release rate, but instead provide a release pattern that approximates square-root-of-time kinetics in which the total amount of drug released is approximately proportional to the square root of the elapsed time. With this release pattern in an aqueous medium, much of the drug in the matrix of many of these formulations is released into an aqueous medium within the first hour.

The benefits of a constant release rate with regard to prolonging therapeutic efficacy while minimizing side effects are well established. It is well known in the art that a nearly constant release rate that simulates zero order kinetics can be obtained by surrounding a tablet core with a membrane or coating. The membranes or coatings described in the art are typically 1-5% of the weight of the tablet. Unfortunately, swelling of the tablet can disrupt the membrane and change the kinetics considerably from zero order. U.S. Pat. No. 4,892,742, issued Jan. 9, 1990 (assignee: Hoffman-La Roche Inc.; inventor: Shah) discloses a tablet consisting of:

1) a core consisting of 5-35% of a water insoluble polymer matrix and 65-95% of a water soluble active ingredient; and
2) a membrane coating comprising 5-10% of the weight of the tablet and consisting of a rate-controlling polymer.

The preferred coating material is ethyl cellulose or a plasticized ethyl cellulose and is a typical controlled release coating for a tablet. The lack of swelling of these membranes and the insoluble core allow the membrane coating to remain intact throughout the release process without breakage, thereby preventing exposure of the core. Without swelling to a minimal size, neither gastric retention of the tablet nor sustained delivery of the active ingredient to the upper gastrointestinal (GI) tract would be achieved.

U.S. Pat. No. 4,629,620, issued Dec. 16, 1986 (assignee: AB Ferrosan; inventor: Lindahl), describes membrane-coated sustained-release tablets where the membrane is an insoluble polymer containing pore-forming agents. Like the tablets and membrane coatings of the Shah patent (U.S. Pat. No. 4,892,742), the tablets and membranes of the Lindahl patent are non-swelling and are not retained in the upper GI tract.

U.S. Pat. No. 5,500,227, issued Mar. 19, 1996 (assignee: Euro-Celtique, S. A.; inventor: Oshlack) discloses the use of a controlled release tablet that consists of:

1) an immediate release tablet core containing an insoluble drug; and
2) a thin hydrophobic coating material.

This patent does not include any disclosure or suggestion that either the membrane or the tablet swells, and thus the patent does not disclose a manner of confining controlled release to the upper GI tract.

U.S. Pat. No. 4,756,911, issued Jul. 12, 1988 (assignee: E. R. Squibb & Sons, Inc.; inventor: Drost) discloses a controlled release tablet for procainamide hydrochloride consisting of:

1) a core containing about 70% (on a weight basis) of the drug, from 5 to 15% by weight of the hydrocolloid gelling agent, hydroxypropylmethyl cellulose, and from 0 to 8% of non-swellable binders; and
2) a water permeable coating film comprised of a mixture of at least one hydrophobic and one hydrophilic polymer.

This patent teaches that the entry of water through the film coating causes the membrane to peel off in 2 to 4 hours after ingestion of the tablet. Drug release proceeds from the core alone.

U.S. Pat. No. 4,891,223, issued Jan. 2, 1990 (assignee: Air Products and Chemicals, Inc.; inventor: Ambegaonkar) discloses compositions containing:

1) an active ingredient that is soluble in the release medium;
2) an inner coating that is water soluble and swellable; and
3) a second outer coating that is water insoluble.

The second outer coating is disclosed as being able to stretch sufficiently to remain in contact with the inner layer, but the second outer coating still may limit the swelling of the composition. The invention described involves controlled-release beads rather than tablets and are far below the size that is necessary to confine release of the active ingredient to the upper GI tract.

The prior art also includes disclosures of multilayer tablets designed to provide release profiles that are intermediate between square-root-of time and zero-order. This prior art is listed below. The multi-layered tablets disclosed in the these patents may swell sufficiently to allow controlled delivery to the upper GI tract, but they do not include a swelling outer layer that fully encloses a core. The outer layers are only partial, discontinuous coatings and thus are not subjected to the large strains that are caused by differential swelling.

U.S. Pat. No. 5,783,212, issued Jul. 21, 1998 (assignee: Temple University; inventor: Fassihi) discloses a three-layer tablet, i.e., a core with a partial coating on only two sides, described as:
1) a drug layer consisting of a swellable, erodible polymer; and
2) two barrier layers comprising swellable, erodible polymers that erode and swell faster than the drug layer.

There is no disclosure or suggestion that the swelling and erosion are matched among the three layers, nor is there any recognition that the drug layer swells faster. There is no disclosure of a swelling membrane or any recognition of the loss of control over the release rate caused by a disrupted membrane.

U.S. Pat. No. 5,549,913, issued Aug. 27, 1996 (assigness: Inverni Della Beffa, S.p.A.; inventor: Colombo), teaches the use of a three-layer tablet where:
1) two external layers, each covering only one side, comprised of hydrophilic swelling polymers and at least one of which contains drug; and
2) an interposing layer controlling the release of the drug.

In this multilayer tablet, the drug is released not through a swelling membrane or coating, but instead through an erodible or soluble layer.

Conte et al., in *Biomaterials* 17(1996):889-896, disclose two- and three-layer tablets with barrier layers that swell or erode. These barrier layers are described as partial coatings and as such do not form barriers that must remain intact under the pressure arising from cores surrounded by coatings that swell at different rates.

Published international application WO 99/47128, published Sep. 23, 1999 (applicant: Bristol-Myers Squibb; inventor: Timmins) discloses a pharmaceutical tablet consisting of:
1) an inner phase containing drug and an extended release material; and
2) an outer phase that is continuous and comprised of an extended release material;

the inner phase being dispersed throughout the outer phase. The extended release materials described in WO 99/47128 can swell substantially to confine delivery to the upper GI tract. The outer continuous phase is a dispersion and not a coating or membrane. The drug release profiles resulting from this invention consequently deviate substantially from zero-order and actually exhibit a release profile that is proportional to the square root of time.

One method of prolonging the release of a highly watersoluble drug is disclosed in International Patent Application Publication No. WO 96/26718, published Sep. 6, 1996 (applicant: Temple University; inventor: Kim). The method disclosed in WO 96/26718 is the incorporation of the drug into a polymeric matrix to form a tablet that is administered orally. The polymer is water-swellable yet erodible in gastric fluids, and the polymer and the proportion of drug to polymer are chosen such that:
(i) the rate at which the polymer swells is equal to the rate at which the polymer erodes, so that the swelling of the polymer is continuously held in check by the erosion, and zero-order release kinetics (constant delivery rate) of the drug from the matrix are maintained;
(ii) the release of drug from the matrix is sustained over the full erosion period of the polymer, the tablet therefore reaching complete dissolution at the same time that the last of the drug is released; and
(iii) release of the drug from the matrix is extended over a period of 24 hours.

A key disclosure in WO 96/26718 is that to achieve the release of drug in this manner, the polymeric matrix must be a polymer of low molecular weight. If, by contrast, a polymer of high molecular weight is used and the swelling rate substantially exceeds the erosion rate, the lack of erosion will prolong even further the delivery of the drug residing close to the center of the tablet and even prevent it from being released. Thus, there is no disclosure in WO 96/26718 that a drug of high water solubility can be released from a high molecular weight polymer in a period of time substantially less than 24 hours, or that any advantage can be obtained by the use of a polymer that does not erode as quickly as it swells. This is particularly significant since any tablet, including swollen tablets, will pass from the stomach after the termination of the fed mode, which typically lasts for only 4 to 6 hours. Moreover, this patent does not teach the use of a membrane or coating, much less one that swells and stays in contact with the core throughout the release of the drug.

In many cases, the passage of a drug from the stomach into the small intestine while the drug is still in a tablet or other dosage form raises problems that lower the therapeutic efficacy of the drug, due to either the absence of the favorable conditions in the stomach, the exposure to unfavorable conditions in the colon, or both.

For example, most orally administered antibiotics are capable of altering the normal flora of the gastrointestinal tract, and particularly the flora of the colon. One result of these alterations is the overgrowth of the organism *Clostridium difficile*, which is a serious adverse event since this organism releases dangerous toxins. These toxins can cause pseudomembranous colitis, a condition that has been reported as a side effect of the use of many antibiotics due to passage of the antibiotics from the stomach through the GI tract to the small intestine. In its milder forms pseudomembranous colitis can cause mild nausea and diarrhea, while in its stronger forms it can be life-threatening or fatal. Examples of antibiotics that pose this type of threat are amoxicillin, cefuroxime axetil, and clindamycin. Cefuroxime axetil (i.e., the axetil ester of cefuroxime), for example, becomes active when hydrolyzed to free cefuroxime, but when this occurs prior to absorption, damage to essential bacterial flora can occur. Hydrolysis to the active form typically occurs in the tissues into which the ester has been absorbed, but if the ester reaches the lower intestine, enzymes in the lower intestine cause the hydrolysis to occur in the intestine itself, which not only renders the drug unabsorbable but also converts the drug to the active form where its activity alters the flora. Further examples are clarithromycin, azithromycin, ceftazidime, ciprofloxacin, and cefaclor. A goal of the present invention is to avoid antibiotic-induced overgrowth of the lower intestinal flora by administering antibiotics, regardless of their level of solubility, in a manner that confines their delivery to the stomach and upper small intestine.

A class of drugs that suffer a loss of benefit from rapid initial release are those that are susceptible to degradation by exposure to gastric fluid, either due to the action of gastric enzymes or as the result of low solution pH. One example of such a drug is topiramate, a drug that is used for the treatment of epilepsy. Topiramate is absorbed most rapidly in the upper GI tract, but when made available at this site, it is hydrolyzed by the acidic environment of the stomach. Avoidance of this high rate of hydrolysis requires a dosage form that does not expose the drug to the acidic environment for an extended period.

A class of drugs that suffer a loss of benefit when allowed to pass into the small intestine are those that are absorbed only in the upper GI tract and suffer from incomplete absorption or from wide differences in absorption, both within a single patient and between different patients. One example of such a drug is cyclosporine, a drug of low solubility that is used as an immunosuppressant to reduce organ rejection in transplant surgery. In addition to its low solubility, cyclosporine has a low absorption rate of about 30% on average, together with wide absorption variability ranging from as little as 5% in some patients to as much as 98% in others. The variability is attributable in part to differences among the various disease states existing in the patients to whom the drug is administered, and in part to differences in the length of time between the transplant surgery and the administration of the drug. The variability can also be attributed to the poor aqueous solubility of the drug, variations in the gastric emptying, variations in the length of time required for intestinal transit between the stomach and the colon, variations in mesenteric and hepatic blood flow, variations in lymph flow, variations in intestinal secretion and fluid volume, variations in bile secretion and flow, and variations in epithelial cell turnover.

Another class of drugs that suffer a loss of benefit when allowed to pass into the small intestine are drugs that are susceptible to degradation by intestinal enzymes. The degradation occurs before the drug can be absorbed through the intestinal wall, leaving only a fraction of the administered dose available for the intended therapeutic action. An example of such a drug is the pro-drug doxifluridine (5'-deoxy-5-fluouridine (dFUR)). The activity of this pro-drug depends on its activation to 5-fluorouracil by pyrimidine nucleoside phosphorylases. These enzymes are found in tumors as well as in normal tissues, and their activity in tumor cells is more than twice their activity in normal tissue. In addition, these enzymes demonstrate their highest activity in the large intestine. When doxifluridine is administered orally, it risks being converted to 5-fluorouracil in the intestine before it reaches the tumors. 5-Fluorouracil is much more toxic than doxifluridine and causes intestinal toxicity (nausea and diarrhea) and severe damage to the intestinal villi. Other drugs that can produce a similar effect upon reaching the colon are cyclosporine and digoxin.

A further class of drugs whose effectiveness declines when the drugs are allowed to pass into the large intestine are those that are susceptible to inactivation by drug transporters that reside in lower gastrointestinal tract enterocytes. The inactivation occurs before the drug penetrates the intestinal wall, leaving only a fraction of the administered dose available for the intended therapeutic action. One example of a drug transporter is the p-glycoprotein efflux system, in which a p-glycoprotein acts as an absorption barrier to certain drugs that are substrates for the p-glycoprotein. The barrier acts by attaching to these drugs and transporting them drug back into the lumen, e.g., the duodenum, jejunum/ileum or colon, from which they were absorbed, or by preventing them from being absorbed at all. This restriction of the drug to the interior of the GI tract is effectively an inactivation of the drug if the drug must pass out of the GI tract into the bloodstream to be effective. Thus, while the p-glycoprotein efflux system is useful in many respects, such as preventing toxic compounds from entering the brain, it interferes with the efficacy of certain drugs whose absorption is necessary in achieving the therapeutic effect. The p-glycoprotein concentration is lowest in the stomach and increases in concentration down the GI tract to the colon where the p-glycoprotein is most prevalent. These drugs therefore would benefit from controlled release over an extended period into the upper GI tract where p-glycoprotein is lowest. Cyclosporine is an example of a drug of low solubility that is susceptible to inactivation by the p-glycoprotein efflux system, in addition to its susceptibility to degradation by colonic bacterial enzymes. Other examples of drugs that are susceptible to the p-glycoprotein efflux system are the anti-cancer drug paclitaxel, ciprofloxacin, and the HIV protease inhibitors saquinavir, ritonavir, and nelfinavir.

A still further class of drugs that suffer from loss of effectiveness when not fully absorbed before reaching the colon are drugs that require an acidic environment for effective bioavailability. For certain drugs, the pH at a given site within the GI tract is an essential determinant of the bioavailability of the drug, since the solubility of the drug varies with pH. The stomach has a low pH and thus creates an acidic environment, while the small intestine has a higher pH, creating a slightly acidic to alkaline environment. Some drugs achieve bioavailability only when ionized by the acidic environment of the stomach. Other drugs are more bioavailable in a non-ionized state. Acidic drugs that have a low pK, for example, are in the neutral form in the stomach, and those that are more bioavailable in this state are preferentially absorbed in the stomach or upper duodenum. Examples of highly soluble drugs that meet this description are esters of ampicillin. Examples of low solubility drugs that behave similarly are iron salts, digoxin, ketoconazole, fluconazole, griseofulvin, itraconazole, and micoconazole. Iron salts are used in the treatment of the various forms of anemia, digoxin is used in the treatment of heart disease, and ketoconazole is used in the treatment of systemic fungal infections such as candidiasis, canduria, blastomycosis, coccidiomycosis, histoplasmosis, chronomycosis, and pacococcidiomycosis. Still further drugs that are more absorbable in the neutral form that is maintained at low pH are those whose molecular structure contains at least one group that becomes ionized in the pH range of 5 through 8, which is the pH range encountered in the small intestine and the region of the colonic junction. In addition, zwitterionic drugs may be better absorbed in a charged form that is present in the acidic environment of the stomach or the duodenal cap. The bioavailability of all of these drugs can be maximized by confining them to the acidic environment of the stomach while controlling their release rate to achieve an extended release profile.

A still further example of drugs that lose their efficacy upon reaching the lower portions of the GI tract are drugs that are soluble in an acidic environment but insoluble in an alkaline or neutral environment. The HIV protease inhibitor nelfinavir mesylate is one example of such a drug. Portions of the drug that are undissolved cannot be absorbed. Portions that are dissolved but not yet absorbed when they pass from the stomach into the small intestine may undergo precipitation and loss of their therapeutic benefit. This is confirmed by the fact that the presence of food in the GI tract substantially increases the absorption of orally administered nelfinavir. Peak plasma concentration and area under the plasma concentration-time curve of nelfinavir are two to three times greater when doses are administered with or following a meal. This is believed to be due at least in part to enhanced retention of the drug in the stomach.

SUMMARY OF THE INVENTION

The present invention resides in a controlled-release dosage form that releases a drug at a rate that approaches zero-order, i.e., a release rate that is substantially constant over time for a period of several hours within the early part of the release profile of the drug, the dosage form substantially confining the release of the drug to the upper GI tract. The dosage form is a dual-matrix configuration, one matrix forming a core of polymeric material in which drug is dispersed and the other matrix forming a casing that surrounds and fully encases the core, the casing being of polymeric material that swells upon imbibition of water (and hence gastric fluid) to a size large enough to promote retention in the stomach during the fed mode, the shell and core being configured such that the drug contained in the core is released from the dosage form by diffusion through the shell. The shell is of sufficient thickness and strength that it is not disrupted by the swelling and remains intact during substantially the entire period of drug release.

This dosage form offers benefits to each of the various types of drugs addressed above. For drugs such as amoxicillin, cefuroxime axetil, clindamycin, and others that tend to cause overgrowth of flora in the lower GI tract, the dosage form of this invention confines the delivery of the drug to the stomach and upper small intestine in a slow, continuous manner. Drugs such as topiramate that are degraded by the gastric enzymes or by the low gastric pH are released more slowly and are protected from the degradation until they are released. Drugs such as cyclosporine that are absorbed only at locations high in the GI tract and whose absorption varies widely among individuals benefit by the dosage form of this invention by being released with less patient-to-patient variability and by being retained in the regions where they are most effectively absorbed. Drugs such as doxifluridine, cyclosporine, and digoxin that are degradable by intestinal enzymes are delivered with less degradation by concentrating their absorption in the stomach. Drugs that are influenced by inactivators such as α-glycoproteins in the lower GI tract are protected against such inactivation by concentrating their release to the upper GI tract. Drugs that are more bioavailable in an acidic environment are more effectively absorbed by concentrating their release to the acidic environment of the stomach, and drugs that tend to lose solubility in an alkaline environment are enhanced by the acidic environment in the upper GI tract. Other examples will be readily apparent to those knowledgeable in the nature and characteristics of drugs.

While both the core and the shell may be water-swellable, the water-swellability of the shell is a characteristic feature of this invention and extends to all embodiments of the invention. The polymeric material of the shell may be erodible as well as swellable, but when an erodible polymer is used, the polymer is one whose erosion rate is substantially lower than the swelling rate. As a result, drug from the core passes through the shell primarily by diffusion in preference to release of the drug by erosion or dissolving of the shell. A further characteristic feature of the invention that extends to all embodiments is the inclusion of drug in the core, but a quantity of drug may also be contained in the shell or applied as a coating to the outside of the shell. This is useful in dosage forms that are designed to provide an initial high rate of drug delivery of short duration or an initial immediate release of the drug, followed by a slow continuous rate over an extended period of time. When drug is present in both the core and the shell, the drug:polymer weight ratio in the shell is substantially less than the drug:polymer weight ratio in the core. This invention further extends to dosage forms that contain a combination of two or more drugs in a single dosage form, where either both drugs are present throughout the dosage form or one drug is dispersed in the core and the other in the shell.

These and other features, characteristics, and embodiments of the invention will be apparent from the description that follows.

BRIEF DESCRIPTION OF THE DRAWING

The attached FIGURE is a plot of the excretion rate of metformin hydrochloride as a function of time from two dosage forms, one of which is in accordance with this invention.

DETAILED DESCRIPTION OF THE INVENTION AND SPECIFIC EMBODIMENTS

Figure 1:
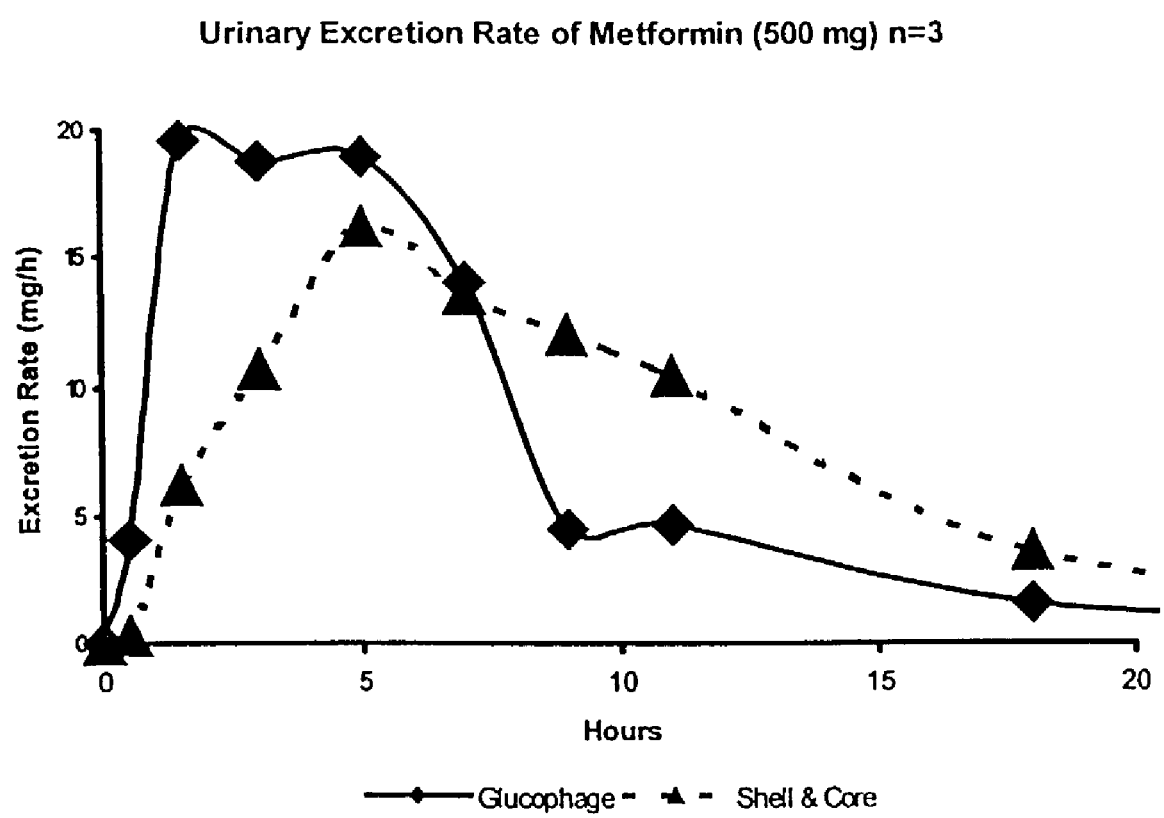

Water-swellable polymers useful in the preparation of the dosage form of this invention include polymers that are nontoxic and, at least in the case of the shell, polymers that swell in a dimensionally unrestricted manner upon imbibition of water and hence of gastric fluid. The core polymer may also be a swelling polymer, and if so, compatible polymers will be selected that will swell together without disrupting the integrity of the shell. The core and shell polymers may be the same or different, and if the same, they may vary in molecular weight, crosslinking density, copolymer ratio, or any other parameter that affects the swelling rate, so long as any swelling occurring in the core causes substantially no splitting of the shell. Examples of suitable polymers are:

- cellulose polymers and their derivatives including, but not limited to, hydroxymethyl cellulose, hydroxyethyl cellulose, hydroxypropyl cellulose, hydroxypropylmethyl cellulose, carboxymethylcellulose, and microcrystalline cellulose
- polysaccharides and their derivatives
- polyalkylene oxides
- polyethylene glycols
- chitosan
- poly(vinyl alcohol)
- xanthan gum
- maleic anhydride copolymers
- poly(vinyl pyrrolidone)
- starch and starch-based polymers
- maltodextrins
- poly(2-ethyl-2-oxazoline)
- poly(ethyleneimine)
- polyurethane hydrogels
- crosslinked polyacrylic acids and their derivatives Further examples are copolymers of the polymers listed above, including block copolymers and graft polymers. Specific examples of copolymers are PLURONIC® and TECTONIC®, which are polyethylene oxide-polypropylene oxide block copolymers available from BASF Corporation, Chemicals Div., Wyandotte, Mich., USA. Further examples are hydrolyzed starch polyacrylonitrile graft copolymers, commonly known as "Super Slurper" and available from Illinois Corn Growers Association, Bloomington Ill., USA.

The term "cellulose" is used herein to denote a linear polymer of anhydroglucose. Preferred cellulosic polymers are alkyl-substituted cellulosic polymers that ultimately dissolve in the GI tract in a predictably delayed manner. Preferred alkyl-substituted cellulose derivatives are those substituted with alkyl groups of 1 to 3 carbon atoms each. In terms of their viscosities, one class of preferred alkyl-substituted celluloses are those whose viscosities are within the range of about 3 to about 110,000 centipoise as a 2% aqueous solution at 25° C. Another class are those whose viscosities are within the range of about 1,000 to about 5,000 centipoise as a 1% aqueous solution at 25° C. Particularly preferred alkyl-substituted celluloses are hydroxyethyl cellulose and hydroxypropyl methylcellulose. Presently preferred hydroxyethyl celluloses are NATRASOL® 250HX and 250HHX NF (National Formulary), available from Aqualon Company, Wilmington, Del., USA.

Of the polyalkylene oxides that are useful in the dosage forms of this invention, particularly preferred examples are poly(ethylene oxide) and poly(propylene oxide). Poly(ethylene oxide) is a linear polymer of unsubstituted ethylene oxide. Poly(ethylene oxide) polymers having viscosity-average molecular weights of about 2,000,000 and higher are preferred. More preferred are those with viscosity-average molecular weights within the range of about 2,000,000 to about 10,000,000, and even more preferred are those with viscosity-average molecular weights within the range of about 4,000,000 to about 8,000,000. Poly(ethylene oxide)s are often characterized by their viscosity in solution. For purposes of this invention, a preferred viscosity range is about 500 to about 500,000 centipoise for a 2% aqueous solution at 25° C. Three presently preferred poly(ethylene oxide)s are:

POLYOX® NF, grade WSR Coagulant, molecular weight 5 million
POLYOX® grade WSR 301, molecular weight 4 million
POLYOX® grade WSR 303, molecular weight 7 million
POLYOX® grade WSR N-60K, molecular weight 2 million All four are products of Union Carbide Chemicals and Plastics Company Inc. of Danbury, Conn., USA. In certain embodiments of this invention, both the core matrix and the shell matrix are poly(ethylene oxide), and the poly(ethylene oxide) used for the core has a higher molecular weight than the poly(ethylene oxide) used for the shell. A preferred range of the viscosity-average molecular weight ratio (core:shell) is from about 1.15:1 to about 2.5:1. In another embodiment, the shell may have a higher molecular weight poly(ethylene oxide) than the core. For this embodiment the preferred range of the viscosity-average molecular weight ratio (core:shell) is from about 0.2:1 to about 1:1.

Polysaccharide gums may be either natural and modified (semi-synthetic). Examples are dextran, xanthan gum, gellan gum, welan gum and rhamsan gum. Xanthan gum is preferred. Alginates including, but not limited to, sodium and calcium alginates may also be used.

Of the crosslinked polyacrylic acids, the preferred types are those with a viscosity ranging from about 4,000 to about 40,000 centipoise for a 0.5% aqueous solution at 25° C. Three presently preferred examples are CARBOPOL® NF grades 971P, 974P and 934P (BFGoodrich Co., Specialty Polymers and Chemicals Div., Cleveland, Ohio, USA). Further examples are polymers known as WATER LOCK®, which are starch/acrylates/acrylamide copolymers available from Grain Processing Corporation, Muscatine, Iowa, USA.

The rate of release of drug from the core and the linearity of the amount released vs. time curve (i.e., the closeness of the release profile to zero-order) will vary to some degree with the thickness of the shell. In most cases, best results will be achieved with a shell having a thickness that is at least about 0.5% of the longest linear dimension of the dosage form. In preferred embodiments, the shell thickness is from about 1% to about 60% of the longest linear dimension of the dosage form. In further preferred embodiments, the shell thickness is from about 1.5% to about 45% of the longest linear dimension, and in the most preferred embodiments, the shell thickness is from about 2% to about 30% of the longest linear dimension.

The drug that is contained in the dosage form for controlled release may be any chemical compound, complex or composition that is suitable for oral administration and that has a beneficial biological effect, preferably a therapeutic effect in the treatment of a disease or an abnormal physiological condition. Examples of high solubility drugs to which this invention is applicable are metformin hydrochloride, vancomycin hydrochloride, captopril, lisinopril, erythromycin lactobionate, ranitidine hydrochloride, sertraline hydrochloride, ticlopidine hydrochloride, baclofen, amoxicillin, cefuroxime axetil, cefaclor, clindamycin, levodopa, doxifluridine, thiamphenicol, tramadol, fluoxitine hydrochloride, ciprofloxacin, bupropion, and esters of ampicillin. Examples low solubility drugs to which this invention is applicable are saguinavir, ritonavir, nelfinavir, clarithromycin, azithromycin, ceftazidime, acyclovir, ganciclovir, cyclosporin, digoxin, paclitaxel, iron salts, topiramate, and ketoconazole. Other drugs suitable for use and meeting the solubility criteria described above will be apparent to those skilled in the art.

Drugs suitable for delivery by the dosage forms of this invention include drugs of low solubility in aqueous media, drugs of moderate solubility, and drugs of high solubility. This invention is of particular interest for drugs whose solubility in water is greater than one part by weight of drug in 25 parts by weight of water. This invention is of further interest for drugs of solubility greater than one part by weight of drug per five parts by weight of water.

The invention is also of use with drugs that have been formulated to include additives that impart a small degree of hydrophobic character to further retard the release rate of the drug into the gastric fluid. One example of such a release rate retardant is glyceryl monostearate. Other examples are fatty acids and salts of fatty acids, one example of which is sodium myristate. The quantities of these additives when present can vary; and in most cases, the weight ratio of additive to drug will range from about 1:20 to about 1:1, and preferably from about 1:8 to about 1:2.

In preferred embodiments of the invention, the drug will be present only in the core of the dosage form and not in the shell. In other embodiments, however, a small amount of the drug will also be present in the shell as a means of releasing an initial amount of the drug at a relatively high rate from the dosage form, before the slow continuous release of drug from the core. In general, the drug:polymer weight ratio in the shell is equal to or less than about 0.5 times the drug:polymer weight ratio in the core. In more preferred embodiments, the drug:polymer weight ratio in the shell is equal to or less than about 0.25 times the drug:polymer weight ratio in the core, and in the most preferred embodiments, the drug:polymer weight ratio in the shell is equal to or less than about 0.05 times the drug:polymer weight ratio in the core.

In some embodiments of this invention, particularly those in which the drug is highly soluble in gastric fluid, the dosage form contains an additional amount of the drug applied as a quickly dissolving coating on the outer surface of the dosage form. This coating is referred to as a "loading dose" and its purpose is to provide, upon ingestion of the dosage form and without first diffusing through a polymer matrix, immediate release into the patient's bloodstream. An optimal "loading dose" is one that is high enough to quickly raise the blood concentration of the drug but not high enough to produce the transient overdosing that is characteristic of highly soluble drugs that are not formulated in accordance with this invention. When a loading dose coating is present, the preferred amounts of drug in the coating relative to the core are those listed in the preceding paragraph with the coating considered as part of the shell.

A film coating may also be included on the outer surface of the dosage form for reasons other than a loading dose. The coating may thus serve an aesthetic function or a protective function, or it may make the dosage form easier to swallow or to mask the taste of the drug.

Turning to the core itself, the weight ratio of drug to polymer in the core may vary. Optimal ratios will depend on the drug solubility, the therapeutic dose, the desired release rate, the polymer and its molecular weight, and the types and amounts of any excipients that may be present in the formulation. The drug:polymer ratio will generally be selected such that at least about 40% of the drug initially in the core remains unreleased one hour after immersion of the dosage form in gastric fluid and substantially all of the drug has been released within about 24 hours after immersion. In preferred embodiments, the ratio will be selected such that at least about 40% of the drug initially in the core remains unreleased two hours after immersion has begun, or more preferably such that at least about 60% of the drug initially in the core remains unreleased two hours after immersion, and most preferably such that at least about 70% of the drug initially in the core remains unreleased two hours after immersion.

The drug loading may also be characterized in terms of the weight percent of drug in the core. In preferred embodiments, the drug constitutes from about 1% to about 98% by weight of the core. In more preferred embodiments, the drug constitutes from about 5% to about 95% by weight of the core, and in the most preferred embodiments, the drug constitutes from about 50% to about 93% by weight of the core.

The dosage forms of this invention may assume a variety of forms, shapes and sizes, provided that the shell upon imbibing gastric fluid swells to a size that promotes the retention of the dosage form in the upper GI tract. Preferred dosage forms are tablets and capsules. Tablets in accordance with this invention consist of an inner continuous solid core which may be porous but is a coherent mass for at least a portion of the time that the tablet is in contact with gastric fluid, surrounded by a continuous solid shell whose inner surface is in full contact with the outer surface of the core and which has the attributes of the shell of this invention as described above. Capsules in accordance with this invention consist of a core made up of one or more particles or tablets (of uniform or single-matrix construction) loosely retained in an unconnected enclosure which serves as the shell and has the attributes of the shell of this invention as described above. A shell may also be constructed by first forming a polymer film and then sealing the film around the core, possibly by heat shrinking. Still further methods include overcoating or dipping of the core in a shell-forming solution or suspension.

Tablets that include a shell as part of the tablet, i.e., a shell that is in full contact with the outer surface of the core, are preferred, and can be prepared by a two-stage tabletting method. The first stage is the preparation of the core, which can be achieved by conventional techniques, such as mixing, comminution, and fabrication techniques readily apparent to those skilled in the manufacture of drug formulations. Examples of such techniques are:

(1) Direct compression using appropriate punches and dies, such as those available from Elizabeth Carbide Die Company, Inc., McKeesport, Pa., USA. The punches and dies are fitted to a suitable rotary tabletting press, such as the Elizabeth-Hata single-sided Hata Auto Press machine, with either 15, 18 or 22 stations, and available from Elizabeth-Hata International, Inc., North Huntington, Pa., USA.;

(2) Injection or compression molding using suitable molds fitted to a compression unit, such as those available from Cincinnati Milacron, Plastics Machinery Division, Batavia, Ohio, USA;.

(3) Granulation such as, but not limited to, fluid bed or high shear granulation or roller compaction, followed by compression; and (4) Extrusion of a paste into a mold or to an extrudate to be cut into lengths.

The second stage of the preparation is the formation of the shell. This can be accomplished by any of steps (1), (2), or (3) performed directly over the core. Advanced tablet presses are available that include pick-and-place functions that are readily adaptable to performing the sequential operations needed to form both the core and the shell.

When particles are made by direct compression, the addition of lubricants may be helpful and is sometimes important to promote powder flow and to prevent capping of the particle (the breaking off of a portion of the particle) when the pressure is relieved. Useful lubricants are magnesium stearate (in a concentration of from 0.25% to 3% by weight, preferably about 1% or less by weight, in the powder mix), and hydrogenated vegetable oil (preferably hydrogenated and refined triglycerides of stearic and palmitic acids at about 1% to 5% by weight, most preferably about 2% by weight). Additional excipients may be added to enhance powder flowability, tablet hardness, and tablet friability and to reduce adherence to the die wall.

As indicated above, the dosage forms of the present invention find their greatest utility when administered to a subject who is in the digestive state, which is also referred to as the postprandial or "fed" mode. The postprandial and interdigestive (or "fasting") modes are distinguishable by their distinct patterns of gastroduodenal motor activity which determine the gastric retention or gastric transit time of the stomach contents.

In the interdigestive mode, the fasted stomach exhibits a cyclic activity called the interdigestive migrating motor complex (IMMC). The cyclic activity occurs in four phases:

Phase I is the most quiescent, lasts 45 to 60 minutes, and develops few or no contractions.

Phase II is marked by the incidence of irregular intermittent sweeping contractions that gradually increase in magnitude.

Phase III, which lasts 5 to 15 minutes, is marked by the appearance of intense bursts of peristaltic waves involving both the stomach and the small bowel.

Phase IV is a transition period of decreasing activity which lasts until the next cycle begins.

The total cycle time of the interdigestive mode is approximately 90 minutes and thus, powerful peristaltic waves sweep out the contents of the stomach every 90 minutes. The IMMC may function as an intestinal housekeeper, sweeping swallowed saliva, gastric secretions, and debris to the small intestine and colon, preparing the upper tract for the next meal while preventing bacterial overgrowth. Pancreatic exocrine secretion of pancreatic peptide and motilin also cycle in synchrony with these motor patterns.

The postprandial or fed mode is normally induced by food ingestion, and begins with a rapid and profound change in the motor pattern of the upper GI tract, the change occurring over a period of 30 seconds to one minute. The stomach generates 3-4 continuous and regular contractions per minute, similar to those of the interdigestive mode but of about half the amplitude. The change occurs almost simultaneously at all sites of the GI tract, before the stomach contents have reached the distal small intestine. Liquids and small particles flow continuously from the stomach into the intestine. Contractions of the stomach result in a sieving process that allows liquids and small particles to pass through a partially open pylorus. Indigestible particles greater than the size of the pylorus are retropelled and retained in the stomach. Particles exceeding about 1 cm in size are thus retained in the stomach for approximately 4 to 6 hours. The dosage form of the present invention is designed to achieve the minimal size through swelling following ingestion during the fed mode.

The postprandial or fed mode can also be induced pharmacologically, by the administration of pharmacological agents that have an effect that is the same or similar to that of a meal. These fed-mode inducing agents may be administered separately or they may be included in the dosage form as an ingredient dispersed in the shell, in both the shell and the core, or in an outer immediate release coating. Examples of pharmacological fed-mode inducing agents are disclosed in co-pending U.S. patent application Ser. No. 09/432,881, filed Nov. 2, 1999, entitled "Pharmacological Inducement of the Fed Mode for Enhanced Drug Administration to the Stomach," inventors Markey, Shell, and Berner, the contents of which are incorporated herein by reference.

The following examples are offered by way of illustration rather than limitation.

Example 1

Compressed Core-and-Shell Tablets of Metformin Hydrochloride

This example illustrates the preparation and release rate behavior of a tablet in accordance with the invention, with a 600-mg core and a 200-mg shell, both of poly(ethylene oxide) and additionally containing metformin hydrochloride in the core only, in a quantity amounting to 62.5% by weight of the core. The term "compressed core-and-shell tablet" is used herein to denote a tablet formed by first compressing the core in a tablet press from a powdered mixture and then using a suitable tablet press to compress another powdered mixture over the core to form the shell. This is distinct from methods of forming a capsule.

To prepare the core, a powder blend was prepared by mixing together metformin hydrochloride (9.374 parts by weight), POLYOX 301 (molecular weight approximately 4,000,000, 5.478 parts by weight), and magnesium stearate (0.151 parts by weight). A 600-mg portion of the mixture was placed on a Carver Auto C Press and compressed at 2500 lb pressure (11,100 Newtons) with a zero-second dwell time and pump speed set at 100%, using a modified capsule die set measuring 0.274×0.725 inch (0.70×1.84 cm), to form the core. The core thus formed was placed in a tablet die measuring 0.375×0.75 inch (0.95×1.90 cm), and surrounded by POLYOX 303 powder (molecular weight approximately 7,000,000) with between 60 and 68 mg of POLYOX 303 underneath the core and 134 to 137 mg of POLYOX 303 on the sides and on top of the core, for a total shell weight of approximately 200 mg. The core and surrounding polymer were then pressed at 2500 lb pressure (11,100 Newtons).

To estimate the release rate of the resulting shell-encased tablets into gastric fluid, the tablets were placed in modified simulated gastric fluid at pH 1.2 at 37° C., and the release of the metformin into the acid was measured as a function of time using a modified USP Type II (paddle with cones) Dissolution Apparatus rotating at 60 rpm. Metformin released into the solution was detected by reverse-phase HPLC. The amounts released at intervals of 2, 4, 6, and 8 hours are listed in Table I below and demonstrate a release rate that approaches zero order.

TABLE I

Metformin Hydrochloride Release Study

| Time from Start of Test (hours) | Amount Released (Percentage of Total in Core) |
| --- | --- |
| 2 | 20.6 |
| 4 | 41.7 |
| 6 | 58.5 |
| 8 | 70.7 |

Example 2

Compressed Core-and-Shell Tablets of Metformin Hydrochloride

This example is a further illustration of the preparation and release rate characteristics of a metformin hydrochloride tablet in accordance with the invention. The procedure of Example 1 was repeated, using nearly identical quantities of materials, except that the poly(ethylene oxide) used as the core matrix was POLYOX Coagulant (molecular weight approximately 5,000,000) rather than POLYOX 301 (molecular weight approximately 4,000,000). The release rate results are listed in Table II, which shows that the release rate again approached zero order.

TABLE II

Metformin Hydrochloride Release Study

| Time from Start of Test (hours) | Amount Released (Percentage of Total in Core) |
| --- | --- |
| 2 | 17.3 |
| 4 | 37.4 |
| 6 | 55.3 |
| 8 | 69.5 |

Example 3

Compressed Core-and-Shell Tablets of Metformin Hydrochloride

This example is a further illustration of the preparation and release rate characteristics of a metformin hydrochloride tablet in accordance with the invention, similar to that of Examples 1 and 2. In this example, however, metformin hydrochloride constituted 83.3% by weight of the core (and present only in the core, as in Examples 1 and 2), and the higher molecular weight poly(ethylene oxide) (POLYOX 303) was used for the core while the lower molecular weight poly(ethylene oxide) (POLYOX 301) was used for the shell. Otherwise, the procedures were essentially the same as those of Examples 1 and 2, except that the die for the outer shell measured 0.3125×0.75 inch (0.79×1.90 cm). The results are listed in Table III, which shows that the release rate again approached zero order.

TABLE III

Metformin Hydrochloride Release Study

| Time from Start of Test (hours) | Amount Released (Percentage of Total in Core) |
|---|---|
| 2 | 21.5 |
| 4 | 45.6 |
| 6 | 65.4 |
| 8 | 78.2 |

Example 4

Compressed Core-and-Shell Tablets of Metformin Hydrochloride

This example is a further illustration of the preparation and release rate characteristics of a metformin hydrochloride tablet in accordance with the invention, the tablet in this case being larger than those of the preceding examples, with a 700 mg core and a 300 mg shell. The drug was 71.3% by weight (present in the core only), and polymer matrices were the same as those of Example 3. The dies in the tabletting press measured 0,274×0.725 inch (0.70×1.84 cm) for the core and 0.375×0.75 inch (0.95×1.90 cm) for the shell.

The results are listed in Table IV, which shows that the release rate again approached zero order.

TABLE IV

Metformin Hydrochloride Release Study

| Time from Start of Test (hours) | Amount Released (Percentage of Total in Core) |
|---|---|
| 2 | 13.2 |
| 4 | 31.2 |
| 6 | 48.3 |
| 8 | 61.5 |

Example 5

Compressed Core-and-Shell Tablets of Metformin Hydrochloride

A further metformin hydrochloride tablet may be prepared in accordance with the invention with a 600 mg core of hydroxypropyl cellulose and a 200-mg shell of poly(ethylene oxide), using a die measuring 0.3125×0.75 inch (0.79×1.90 cm). The metformin hydrochloride (residing only in the core) will amount to 83.3% by weight of the core. The hydroxypropyl cellulose in this example is KLUCEL® HPC HF.

Example 6

Core-Coated Tablets of Metformin Hydrochloride

This example illustrates the preparation and release rate characteristics of a metformin hydrochloride tablet using the same materials as Example 5, except with a 700 mg core and a 300 mg shell, and a drug loading (in the core only) of 71.4% by weight. The results are listed in Table VI, which shows that the release rate again approached zero order.

TABLE VI

Metformin Hydrochloride Release Study

| Time from Start of Test (hours) | Amount Released (Percentage of Total in Core) |
|---|---|
| 2 | 35.5 |
| 4 | 61.3 |
| 6 | 76.0 |
| 8 | 84.4 |

Example 7

Compressed Core-and-Shell Tablets of Metformin Hydrochloride (Ref. NB 36, pp. 31; NB 34, pp. 92-95)

This example illustrates the preparation and release rate characteristics of a metformin hydrochloride tablet similar to those of the preceding examples, except that the shell was constructed of a mixture of poly(ethylene oxide) (of low molecular weight relative to the same polymer in the core) and EUDRAGIT® L100-55 methacrylic polymers (Röhm America, Inc., Piscataway, N.J. USA). The weight ratio of poly(ethylene oxide) to methacrylic polymer in the shell was 1.48:1, the poly(ethylene oxide) in the core was POLYOX 303 (molecular weight 7,000,000) and the poly(ethylene oxide) in the shell was POLYOX 301 (molecular weight 4,000,000). The drug was present in the core only, at 83.3% by weight of the core. The results are listed in Table VII, which shows that the release rate again approached zero order.

TABLE VII

Metformin Hydrochloride Release Study

| Time from Start of Test (hours) | Amount Released (Percentage of Total in Core) |
|---|---|
| 2 | 30.7 |
| 4 | 56.6 |
| 6 | 74.4 |
| 8 | 84.1 |

Example 8

Compressed Core-and-Shell Tablets of Metformin Hydrochloride

This example illustrates the preparation and release rate characteristics of metformin hydrocholoride tablets similar to those of the preceding examples, except that three different polymers blends were used to form the shells of the tablets:
 Shell A Polymer: POLYOX 301
 Shell B Polymer: blend of POLYOX 301 and EUDRAGIT L100-55, POLYOX:EUDRAGIT weight ratio 3.9:1
 Shell C Polymer: blend of POLYOX 301 and KOLLIDON 90F (polyvinylpyrrolidone, BASF AG, Ludwigshafen, Germany), POLYOX:KOLLIDON weight ratio 3.9:1

The core each case was 600 mg and the shell was 200 mg, and the drug (present only in the core) constituted 83.3% by weight of the core. The results are listed In Table VIII, which shows that the release rate approached zero order at early times before the driving was depleted.

TABLE VIII

Metformin Hydrochloride Release Study

| Time from Start of Test (hours) | Amount Released (Percentage of Total in Core) | | |
|---|---|---|---|
| | Shell A | Shell B | Shell C |
| 1 | 15.1 | 11.3 | 15.7 |
| 2 | 34.0 | 29.3 | 38.9 |
| 3 | 55.3 | 45.3 | 54.3 |
| 4 | 82.8 | 54.5 | 60.1 |
| 6 | 93.1 | 61.7 | 63.8 |

Example 9

Compressed Core-and-shell Tablets of Metformin Hydrochloride

This example illustrates the preparation and release rate characteristics of a metformin hydrochloride tablet similar to those of the preceding examples, except with a lower proportion of the shell to core. In particular, the core was 700 mg and the shell was 200 mg. The drug loading in the core was 71.4% by weight (with no drug contained in the shell), the core polymer matrix was POLYOX 303, and the shell polymer matrix was POLYOX 301. The results are listed in Table IX, which shows that the release rate approached zero order.

TABLE IX

Metformin Hydrochloride Release Study

| Time from Start of Test (hours) | Amount Released (Percentage of Total in Core) |
|---|---|
| 2 | 20.3 |
| 4 | 40.2 |
| 6 | 56.7 |
| 8 | 70.8 |

Example 10

Compressed Core-and-Shell Tablets of Metformin Hydrochloride

This example illustrates the preparation and release rate characteristics of metformin hydrocholoride tablets similar to those of the EXAMPLE 9, except using poly(ethylene oxide) of the molecular weight in both the core and the shell. The core in these tablets was 800 mg in size, the shell was 250 mg in size, and the drug loading in the core was 79.2% by weight (with no drug in the shell). The results are listed in Table X, which shows that the release rate approached zero order.

TABLE X

Metformin Hydrochloride Release Study

| Time from Start of Test (hours) | Amount Released (Percentage of Total in Core) |
|---|---|
| 2 | 15.9 |
| 4 | 34.6 |
| 6 | 50.2 |
| 8 | 63.9 |

Example 11

Compressed Core-and-Shell Tablets of Metformin Hydrochloride With Various Polymers This example demonstrates the release rates of metformin hydrochloride tablets in accordance with this invention, using various combinations of polymers for the core and shell. In each case, the core and shell were 600 mg and 200 mg in weight, respectively, each containing 1.0% by weight magnesium stearate, and the drug loading in the core was 83.3% by weight (and no drug in the shell). The apparatus used for measuring the release rate was a USP Type I (10-mesh baskets) Dissolution Apparatus rotating at 100 rpm with 900 mL of modified simulated gastric fluid (at pH 1.2), and the amount of drug released was detected by reverse-phase HPLC. The various polymers used were as follows (all molecular weights are viscosity average molecular weights and are approximate):

POLYOX® 301—poly(ethylene oxide), molecular weight 4,000,000, Union Carbide Corporation, Danbury, Conn., USA POLYOX® 303—poly(ethylene oxide), molecular weight 7,000,000, Union Carbide Corporation, Danbury, Conn., USA POLYOX® Coagulant—poly(ethylene oxide), molecular weight 5,000,000, Union Carbide Corporation, Danbury, Conn., USA NATROSOL® 250 HHX Pharm—hydroxyethyl cellulose, Brookfield viscosity of 1% solution at 25° C.: 3,500-5,500 cps, Hercules, Incorporated, Aqualon Division, Wilmington, Del. USA KLUCEL® HXF—hydroxypropyl cellulose, Brookfield viscosity of 1% solution at 25° C.: 1,500-3,000 cps, Hercules, Incorporated, Aqualon Division, Wilmington, Del. USA The release rate results are shown in Table XI.

TABLE XI

Metformin Hydrochloride Release Study

| Core Polymer | Shell Polymer | Amount of Drug Released (Percentage of Total in Core) | | | |
|---|---|---|---|---|---|
| | | 2 h | 4 h | 6 h | 8 h |
| POLYOX 301 | POLYOX 303 | 30 | 65 | 87 | 96 |
| POLYOX Coagulant | POLYOX 301 | 29 | 63 | 86 | 97 |
| NATROSOL 250 HHX | NATROSOL 250 HHX | 39 | 68 | 86 | 95 |
| KLUCEL HXF | NATROSOL 250 HHX | 29 | 56 | 74 | 86 |

Example 12

Capsules of Metformin Hydrochloride

This example illustrates the preparation and release rate characteristics of a cylindrical capsule in which the capsule shell serves as the shell of the invention, loosely surrounding a compressed tablet that serves as the core containing the drug. The drug used in this preparation was metformin hydrochloride.

The tablet was prepared by blending 3.329 parts by weight of metformin hydrochloride, 0.630 parts by weight of POLYOX 303 and 0.039 parts by weight of magnesium stearate to from a 400-mg core. The blend was pressed into tablet form on a Carver Auto C Press at 1500 lb pressure (6,670 Newtons) with a zero-second dwell time and 100% pump speed using a 15.35×5.6 mm die. To prepare the capsule, POLYOX 301 was melted between two glass plates that had been previously sprayed with mold release (Dry Film PTFE, McMaster-Carr). The dry poly(ethylene oxide) film that was thus formed was cut into rectangles and wrapped around TEFLON® bars to form a 0.25 inch (0.64 cm) diameter cylinder. One end of each cylinder was melt-sealed between two glass plates in a 100° C. oven. One tablet was placed inside each cylinder, and the unsealed end of the cylinder was then melt-sealed. Another set of capsules was prepared by wrapping each tablet in a sheet of the POLYOX 301 film (prepared between glass plates as described above) and pinching the ends of the wrapped film to close the capsule.

The release of the drug from the wrapped capsules (the second set described in the preceding paragraph) into modified simulated gastric fluid at 37° C. was measured as a function of time using an USP Type I (10 mesh baskets) Dissolution Apparatus rotating at 100 rpm. The drug was detected by reverse phase HPLC at 2, 4, 6, and 8 hours. The results are listed the Table XII below, showing a release rate that approaches zero order.

TABLE XII

Metformin Hydrochloride Release Study

| Time from Start of Test (hours) | Amount Released (Percentage of Total in Core) |
|---|---|
| 2 | 0.8 |
| 4 | 11.7 |
| 6 | 32.9 |
| 8 | 59.1 |

Example 13

Compressed Core-and-Shell Tablets of Riboflavin-5'-Phosphate

This example illustrates the preparation and release rate characteristics of a tablet in accordance with invention, in which the drug is riboflavin-5'-phosphate (present only in the core). The core was prepared by compression tabletting and the shell was formed around the core in the same manner, both as described above in Examples 1 through 11. The core in this tablet was 700 mg in weight, the shell was 200 mg in weight, and the drug loading in the core was 11.1% by weight. In addition to the drug, the core formulation contained 60.3% by weight of lactose monohydrate, 27.6% POLYOX 303, and 1.0% magnesium stearate. The shell was POLYOX 301 with 1.0% magnesium stearate. The detection of released riboflavin-5'-phosphate was accomplished by UV spectroscopy.

The release rate results are listed in Table XIII, which shows a release profile that is faster than zero order.

TABLE XIII

Riboflavin-5'-Phosphate Release Study

| Time from Start of Test (hours) | Amount Released (Percentage of Total in Core) |
|---|---|
| 2 | 1.3 |
| 4 | 2.7 |

TABLE XIII-continued

Riboflavin-5'-Phosphate Release Study

| Time from Start of Test (hours) | Amount Released (Percentage of Total in Core) |
|---|---|
| 6 | 4.8 |
| 8 | 8.0 |

Example 14

Compressed Core-and-Shell Tablets of Aspirin

This example illustrates the preparation and release rate characteristics of a tablet in accordance with the invention by the procedures of Examples 1-11 above, in which the drug is aspirin (present only in the core). The core in this tablet was 400 mg in weight, the shell was 200 mg in weight, and the aspirin loading was 81.3% by weight of the core. In addition to the aspirin, the core formulation contained 17.7% POLYOX 303, and 1.0% magnesium stearate. The shell was 39.268% POLYOX 301 and 59.667% EUDRAGIT L110-55 with 1.065% magnesium stearate.

Release rate data were determined by release into 900 mL of acetate buffer at pH 4.5, as specified in the USP method for immediate-release aspirin, and a USP Type I Dissolution Apparatus was used. The released aspirin was detected by reverse-phase HPLC. The results are listed in Table XIV, showing a release rate that approaches zero order.

TABLE XIV

Aspirin Release Study

| Time from Start of Test (hours) | Amount Released (Percentage of Total in Core) |
|---|---|
| 1.5 | 0.90 |
| 3 | 2.62 |
| 4.5 | 4.57 |
| 6 | 6.75 |

Example 15

In Vivo Comparison Study

This example presents a comparison between the release rate characteristics of a compressed core-and-shell tablet of the present invention in which the drug is present only in the core and an immediate-release formulation of the same drug. The drug in each case was metformin hydrochloride, and the two tablets were as follows:

Tablet A: Core: 600 mg, of which 78.33% by weight was metformin hydrochloride, 15.67% by weight was POLYOX 303, 5% miscellaneous excipients present in GLUCOPHAGE® (Bristol-Myers Squibb), and 1% by weight was magnesium stearate Shell: 200 mg, of which 99% by weight was POLYOX 301 and 1% by weight was magnesium stearate Tablet B: GLUCOPHAGE®, Bristol-Myers Squibb, containing 500 mg metformin hydrochloride with 6% miscellaneous excipients Three healthy adult human subjects were each administered one of each of the tablets with 100 mL water in the morning immediately after a standard specified breakfast. A standard specified lunch was taken by each subject. Water was drunk by each subject at a rate of 60 mL per hour. Vital signs (blood pressure and heart rate) and blood samples for glucose measurements were taken prior to dosing, and at 2, 4, and 8 hours after dosing on the first day.

All urine voids were collected from each subject for 72 hours after dosing, following emptying of the bladder prior to dosing. Urine collections were made immediately prior to dosing and at accumulated 0-1, 1-2, 2-4, 4-6, 6-8, 8-10, and 10-12 hours after dosing. Subsequent urine collections were accumulated over 12-hour periods for the next two days. The urine samples were then analyzed for metformin hydrochloride by an HPLC method adapted from that described in Caillé, G., *Biopharm. Drug Dispos.* 14 (1993): 257-263. The results, expressed in terms of the excretion rate of metformin hydrochloride in mg/h vs. time after dosage (in hours), are shown in FIG. 1, where the triangle-shaped points are the data from Tablet A (representing the present invention) and the diamond-shaped points are the data from Tablet B. The Tablet A curve demonstrates a clear advantage over the Tablet B curve by virtue of the lower slope and essentially linear shape of the Tablet A curve up through five hours (with continued delivery through 7 hours). By avoiding an initial burst of metformin, the present invention lessens the occurrence of gastrointestinal and taste disturbances.

The foregoing is offered primarily for purposes of illustration. It will be readily apparent to those skilled in the art that the components, additives, proportions, methods of formulation, and other parameters of the invention can be modified further or substituted in various ways without departing from the spirit and scope of the invention.

What is claimed is:

1. A controlled-release oral drug dosage form for releasing a drug into at least a portion of a region defined by the stomach and the upper gastrointestinal tract, said dosage form comprising:
   (a) a core comprising a first solid polymeric matrix with said drug dispersed therein, and
   (b) a shell encasing said core, said shell comprising a second solid polymeric matrix that swells upon imbibition of water to a size large enough to promote retention in the stomach while the stomach is in a fed mode, and said shell having a drug:polymer weight ratio that is less than that of said core, said shell having a thickness that is at least about 0.5% of the longest linear dimension of said dosage form, said second polymeric matrix being of a material and thickness relative to said core such that when said dosage form is immersed in gastric fluid, said drug is released from said dosage form into said gastric fluid at a controlled rate by diffusion of said drug through said shell during substantially the entire period of drug release such that at least about 40% of said drug remains unreleased one hour after such immersion has begun and substantially all of said drug is released within about twenty-four hours after such immersion has begun, said shell remaining intact during substantially the entire period of drug release, wherein said first solid polymeric matrix and said second polymeric matrix comprise a polymer independently selected from the group consisting of a poly(ethylene oxide), a cross-linked polyacrylic acid, and a hydroxyalkyl-substituted cellulose.

2. A controlled-release oral drug form in accordance with claim 1 in which said drug is dispersed in the shell.

3. A controlled-release oral drug dosage form in accordance with claim 2 in which said core has an outer surface and said shell has an inner surface in full contact with said outer surface of said core.

4. A controlled-release oral drug dosage form in accordance with claim 2 in which said shell thickness is from about 1% to about 60% of the longest linear dimension of said dosage form.

5. A controlled-release oral drug dosage form in accordance with claim 2 in which said shell thickness is from about 1.5% to about 45% of the longest linear dimension of said dosage form.

6. A controlled-release oral drug dosage form in accordance with claim 2 in which said shell thickness is from about 2% to about 30% of the longest linear dimension of said dosage form.

7. A controlled release oral drug dosage form in accordance with claim 2 in which the drug:polymer weight ratio of said shell is equal to or less than about 0.25 times the drug:polymer weight ratio of said core.

8. A controlled release oral drug dosage form in accordance with claim 2 in which the drug:polymer weight ratio of said shell is equal to or less than about 0.05 times the drug:polymer weight ratio of said core.

9. A controlled-release oral drug dosage form in accordance with claim 1 in which said oral drug dosage form is a tablet having a total weight of from about 50 mg to about 5000 mg.

10. A controlled-release oral drug dosage form in accordance with claim 1 in which said oral drug dosage form is a tablet having a total weight of from about 100 mg to about 3000 mg.

11. A controlled-release oral drug dosage form in accordance with claim 2 in which said oral drug dosage form is a tablet having a total weight of from about 500 mg to about 2000 mg.

12. A controlled-release oral drug dosage form in accordance with claim 2 in which said first and second polymeric matrices are formed of polymers independently selected from the group consisting of poly(ethylene oxide), hydroxymethyl cellulose, hydroxyethyl cellulose, hydroxypropyl cellulose, and hydroxypropylmethyl cellulose.

13. A controlled-release oral drug dosage form in accordance with claim 2 in which said first and second polymeric matrices are formed of polymers independently selected from the group consisting of poly(ethylene oxide), hydroxypropylmethyl cellulose, and hydroxyethyl cellulose.

14. A controlled-release oral drug dosage form in accordance with claim 2 in which said first and second polymeric matrices are both poly(ethylene oxide).

15. A controlled-release oral drug dosage form in accordance with claim 2 in which said poly(ethylene oxide) has a molecular weight of at least about 2,000,000.

16. A controlled-release oral drug dosage form in accordance with claim 2 in which said poly(ethylene oxide) has a molecular weight of from about 2,000,000 to about 10,000,000.

17. A controlled-release oral drug dosage form in accordance with claim 2 in which said poly(ethylene oxide) of said first polymeric matrix has a higher molecular weight than said poly(ethylene oxide) of said second polymeric matrix.

18. A controlled-release oral drug dosage form in accordance with claim 2 in which said poly(ethylene oxide) of said first polymeric matrix has a lower molecular weight than said poly(ethylene oxide) of said second polymeric matrix.

19. A controlled-release oral drug dosage form in accordance with claim 2 in which the molecular weight ratio of said poly(ethylene oxide) of said first polymeric matrix to said poly(ethylene oxide) of said second polymeric matrix is from about 1.15:1 to about 2.5:1.

20. A controlled-release oral drug dosage form in accordance with claim 2 in which the amount of said drug in said core is from about 1% to about 98% by weight.

21. A controlled-release oral drug dosage form in accordance with claim 2 in which the amount of said drug in said core is from about 5% to about 95% by weight.

22. A controlled-release oral drug dosage form in accordance with claim 2 in which the amount of said drug in said core is from about 50% to about 93% by weight.

23. A controlled-release oral drug dosage form in accordance with claim 2 in which said second polymeric matrix is of a material and volume relative to said core that at least about 40% of said drug remains unreleased two hours after such immersion has begun.

24. A controlled-release oral drug dosage form in accordance with claim 2 in which said second polymeric matrix is of a material and volume relative to said core that at least about 60% of said drug remains unreleased two hours after such immersion has begun.

25. A controlled-release oral drug dosage form in accordance with claim 2 in which said second polymeric matrix is of a material and volume relative to said core that at least about 70% of said drug remains unreleased two hours after such immersion has begun.

26. A controlled-release oral drug dosage form in accordance with claim 2 in which said drug has a solubility in water of greater than one part by weight of said drug in 25 parts by weight of water.

27. A controlled-release oral drug dosage form in accordance with claim 2 in which said drug has a solubility in water of greater than one part by weight of said drug in ten parts by weight of water.

28. A controlled-release oral drug dosage form in accordance with claim 2 in which said drug is a member selected from the group consisting of metformin hydrochloride, vancomycin hydrochloride, captopril, lisinopril, erythromycin lactobionate, acyclovir, ranitidine hydrochloride, baclofen, sertraline hydrochloride, levodopa, tramadol, and ticlopidine hydrochloride.

29. A controlled-release oral drug dosage form in accordance with claim 1 in which said drug is a member selected from the group consisting of amoxicillin, cefuroxime axetil, cefaclor, clindamycin, clarithromycin, azithromycin, ceftazidine, and ciprofloxacin.

30. A controlled-release oral drug dosage form in accordance with claim 1 in which said drug is a member selected from the group consisting of cyclosporine, digoxin, doxifluridine, and paclitaxel.

31. A controlled-release oral drug dosage form in accordance with claim 1 in which said drug is a member selected from the group consisting of esters of ampicillin, iron salts, digoxin, and ketoconazole.

32. A controlled-release oral drug dosage form in accordance with claim 1 in which said drug is nelfinar mesylate.

33. A controlled-release oral drug dosage form in accordance with claim 1 in which said shell contains substantially none of said drug.

34. A controlled-release oral drug dosage form in accordance with claim 33 in which said core has an outer surface and said shell has an inner surface in full contact with said outer surface of said core.

35. A controlled-release oral drug dosage form in accordance with claim 33 in which said shell thickness is from about 1% to about 60% of the longest linear dimension of said dosage form.

36. A controlled-release oral drug dosage form in accordance with claim 33 in which said shell thickness is from about 1.5% to about 45% of the longest linear dimension of said dosage form.

37. A controlled-release oral drug dosage form in accordance with claim 33 in which said shell thickness is from about 2% to about 30% of the longest linear dimension of said dosage form.

38. A controlled-release oral drug dosage form in accordance with claim 33 in which said oral drug dosage form is a tablet having a total weight of from about 500 mg to about 2000 mg.

39. A controlled-release oral drug dosage form in accordance with claim 33 in which said first and second polymeric matrices are formed of polymers independently selected from the group consisting of poly(ethylene oxide), hydroxymethyl cellulose, hydroxyethyl cellulose, hydroxypropyl cellulose, and hydroxypropylmethyl cellulose.

40. A controlled-release oral drug dosage form in accordance with claim 33 in which said first and second polymeric matrices are formed of polymers independently selected from the group consisting of poly(ethylene oxide), hydroxypropylmethyl cellulose, and hydroxyethyl cellulose.

41. A controlled-release oral drug dosage form in accordance with claim 33 in which said first and second polymeric matrices are both poly(ethylene oxide).

42. A controlled-release oral drug dosage form in accordance with claim 33 in which said poly(ethylene oxide) has a molecular weight of at least about 2,000,000.

43. A controlled-release oral drug dosage form in accordance with claim 33 in which said poly(ethylene oxide) has a molecular weight of from about 2,000,000 to about 10,000,000.

44. A controlled-release oral drug dosage form in accordance with claim 33 in which said poly(ethylene oxide) of said first polymeric matrix has a higher molecular weight than said poly(ethylene oxide) of said second polymeric matrix.

45. A controlled-release oral drug dosage form in accordance with claim 33 in which said poly(ethylene oxide) of said first polymeric matrix has a lower molecular weight than said poly(ethylene oxide) of said second polymeric matrix.

46. A controlled-release oral drug dosage form in accordance with claim 33 in which the molecular weight ratio of said poly(ethylene oxide) of said first polymeric matrix to said poly(ethylene oxide) of said second polymeric matrix is from about 1.15:1 to about 2.5:1.

47. A controlled-release oral drug dosage form in accordance with claim 33 in which said second polymeric matrix is of a material and volume relative to said core that at least about 40% of said drug remains unreleased two hours after such immersion has begun.

48. A controlled-release oral drug dosage form in accordance with claim 33 in which said second polymeric matrix is of a material and volume relative to said core that at least about 60% of said drug remains unreleased two hours after such immersion has begun.

49. A controlled-release oral drug dosage form in accordance with claim 33 in which said second polymeric matrix is of a material and volume relative to said core that at least about 70% of said drug remains unreleased two hours after such immersion has begun.

50. A controlled-release oral drug dosage form in accordance with claim 33 in which said drug has a solubility in water of greater than one part by weight of said drug in 25 parts by weight of water.

51. A controlled-release oral drug dosage form in accordance with claim 33 in which said drug has a solubility in water of greater than one part by weight of said drug in ten parts by weight of water.

52. A controlled-release oral drug dosage form in accordance with claim 33 in which said drug is a member selected from the group consisting of metformin hydrochloride, vancomycin hydrochloride, captopril, lisinopril, erythromycin lactobionate, acyclovir, ranitidine hydrochloride, baclofen, sertraline hydrochloride, levodopa, tramadol, and ticlopidine hydrochloride.

53. A controlled-release oral drug dosage form in accordance with claim 1 comprising two or more drugs.

54. A controlled-release oral drug dosage form in accordance with claim 53 wherein the two or more drugs are present throughout the dosage form.

55. A controlled-release oral drug dosage form in accordance with claim 53 wherein a first drug is dispersed in the core and a second drug is dispersed in the shell.

\* \* \* \* \*